(12) United States Patent
Patterson et al.

(10) Patent No.: US 6,607,555 B2
(45) Date of Patent: Aug. 19, 2003

(54) DELIVERY CATHETER ASSEMBLY AND METHOD OF SECURING A SURGICAL COMPONENT TO A VESSEL DURING A SURGICAL PROCEDURE

(75) Inventors: Frank Patterson, Exeter, NH (US); Howard M. Tanner, Logan, UT (US); Hugh H. Trout, III, Bethesda, MD (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/783,313

(22) Filed: Feb. 15, 2001

(65) Prior Publication Data

US 2002/0026144 A1 Feb. 28, 2002

Related U.S. Application Data

(60) Provisional application No. 60/182,543, filed on Feb. 15, 2000.

(51) Int. Cl.$^7$ ................................................ A61F 2/06
(52) U.S. Cl. ................................ 623/1.23; 604/95.04
(58) Field of Search .......................... 606/119, 120; 604/95.04, 164.12, 164.08, 171, 198, 525, 528; 623/1.23

(56) References Cited

U.S. PATENT DOCUMENTS

| | | |
|---|---|---|
| 3,978,863 A | 9/1976 | Fettel et al. |
| 5,037,421 A | 8/1991 | Boutacoff et al. |
| 5,147,354 A | 9/1992 | Boutacoff et al. |
| 5,462,561 A * | 10/1995 | Voda ........................... 112/169 |
| 5,599,305 A | 2/1997 | Hermann et al. |
| 5,690,117 A | 11/1997 | Gilbert |
| 5,797,905 A | 8/1998 | Fleischman et al. |
| 5,938,696 A | 8/1999 | Goicoechea et al. |
| 5,944,750 A * | 8/1999 | Tanner et al. ................ 606/108 |
| 5,957,940 A * | 9/1999 | Tanner et al. ................ 606/155 |
| 5,997,556 A * | 12/1999 | Tanner ......................... 606/153 |

\* cited by examiner

*Primary Examiner*—Edward K. Look
*Assistant Examiner*—John K Fristoe, Jr.
(74) *Attorney, Agent, or Firm*—Collier Shannon Scott, PLLC; John N. Coulby

(57) ABSTRACT

The present invention is directed to a delivery catheter assembly for advancing a surgical device to a desired location within a vessel during a surgical procedure. The delivery catheter assembly includes an inner sheath assembly through which the surgical device is advanced to the desired location within the vessel. The delivery catheter assembly further includes an outer sheath assembly surrounding the inner sheath assembly. In accordance with the present invention, at least one of the inner sheath assembly and the outer sheath assembly has an angular configuration at a predetermined time during the surgical procedure. The present invention further includes an adjusting assembly for creating the angular configuration of at least one of the inner sheath assembly and the outer sheath assembly. The adjusting assembly may include at least one pull wire positioned within one of the inner sheath and the outer sheath. Furthermore, the inner sheath assembly is movable with respect to the outer sheath assembly. The inner sheath assembly is capable of moving between an extended position and a retracted position at the predetermined time during the surgical procedure.

33 Claims, 9 Drawing Sheets

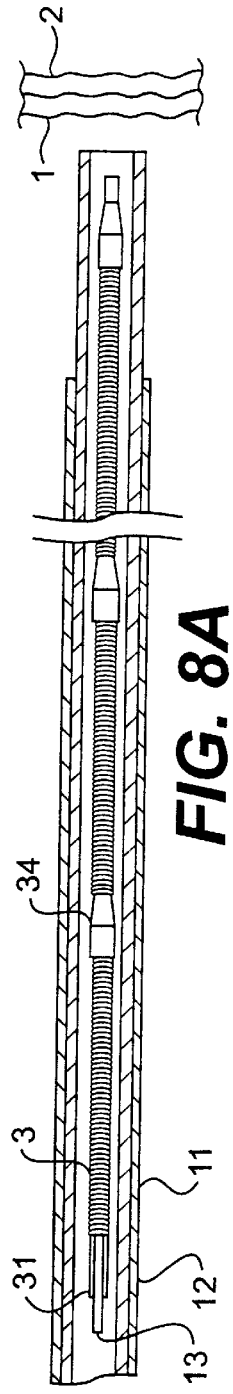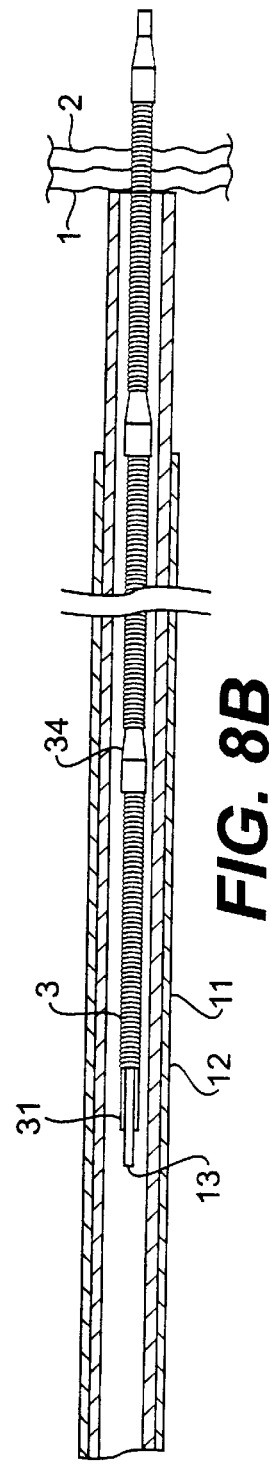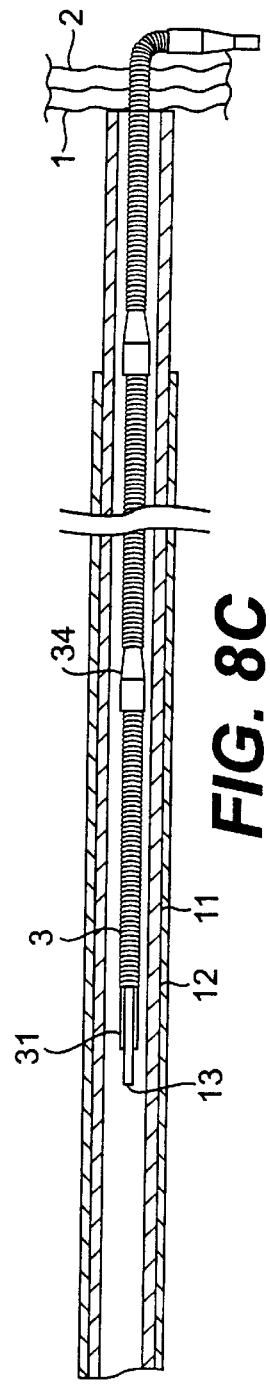

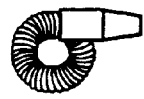
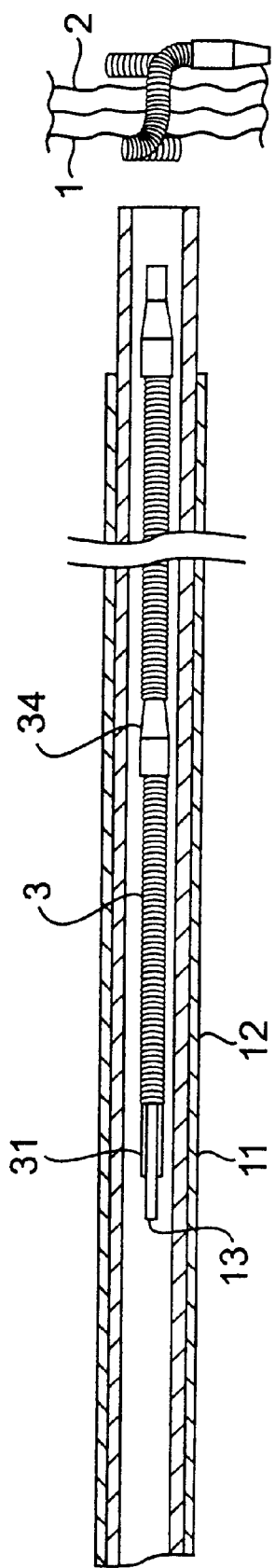
FIG. 8D
FIG. 8E

DELIVERY CATHETER ASSEMBLY AND METHOD OF SECURING A SURGICAL COMPONENT TO A VESSEL DURING A SURGICAL PROCEDURE

CROSS REFERENCE TO RELATED APPLICATIONS

The present invention relates to and claims priority on U.S. Provisional Application Ser. No. 60/182,543, filed on Feb. 15, 2000.

FIELD OF THE INVENTION

The present invention relates to a delivery catheter assembly. In particular, the present invention is directed to a delivery catheter assembly for use in surgical procedures to whereby a first component is secured to a second component using a fastener delivered to the surgical site by the delivery catheter assembly.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta surrounding the aneurysm to ensure attachment of the graft. The neck of the aorta at the cephalad end (i.e., above the aneurysm) is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which to successfully mount a graft. Furthermore, much of the abdominal aorta wall may be calcified which may make it extremely difficult to attach the graft to the wall. Furthermore, the prior art does not disclose surgical devices that can be used during a surgical procedure that address these concerns. Others have developed devices that are not easily manipulated or oriented during intraluminal surgical procedures.

OBJECTS OF THE INVENTION

It is an object of the present invention to provide an assembly for use in connection with securing a surgical component to a vessel during a surgical procedure.

It is another object of the present invention to provide a delivery catheter assembly for delivering and inserting a fastener assembly at a desired location during a surgical procedure.

It is another object of the present invention to provide a delivery catheter assembly that may be easily advanced within a vessel during a surgical procedure.

It is another object of the present invention to provide a procedure for securing a surgical component to a vessel.

It is another object of the present invention to provide an assembly for firmly securing a graft assembly to an aortic wall.

It is another object of the present invention to provide an assembly for use in the repair of an aortic aneurysm.

It is another object of the present invention to provide an apparatus for securing a surgical component to a vessel during a minimally invasive surgical procedure.

It is another object of the present invention to provide a delivery catheter having a tip that is capable of unidirectional deflection.

It is another object of the present invention to provide a delivery catheter having a tip that is capable of multi-directional deflection.

It is another object of the present invention to provide a torqueable delivery catheter.

It is another object of the present invention to provide a delivery catheter having at least one wire assembly embedded within the delivery catheter to permit deflection of the tip of the delivery catheter.

SUMMARY OF THE INVENTION

The present invention is directed to a delivery catheter assembly for advancing a surgical device to a desired location within a vessel during a surgical procedure. The delivery catheter assembly includes an inner sheath assembly through which the surgical device is advanced to the desired location within the vessel. The delivery catheter assembly further includes an outer sheath assembly surrounding the inner sheath assembly. In accordance with the present invention, at least one of the inner sheath assembly and the outer sheath assembly has an angular configuration at a predetermined time during the surgical procedure. The present invention further includes an adjusting assembly for creating the angular configuration of at least one of the inner sheath assembly and the outer sheath assembly. The adjusting assembly may include at least one pull wire positioned within one of the inner sheath and the outer sheath. Furthermore, the inner sheath assembly is movable with respect to the outer sheath assembly. The inner sheath assembly is capable of moving between an extended position and a retracted position at the predetermined time during the surgical procedure.

The present invention is also directed to an assembly for use in securing a surgical component to a vessel during a surgical procedure. The assembly includes a catheter delivery assembly and an insertion assembly. The delivery catheter assembly may include an inner sheath assembly through which the surgical device is advanced to a desired location within the vessel, and an outer sheath assembly surrounding the inner sheath assembly. The insertion assembly may include an assembly for creating an aperture within the surgical component and the vessel such that a fastener assembly may be inserted there through. The assembly may further include an advancing assembly for advancing the delivery catheter assembly to the desired location within the vessel during the surgical procedure. The advancing assembly may include a delivery sheath, wherein the delivery catheter assembly may be slidably received with the delivery sheath.

The assembly of the present invention may also include an inner sheath assembly and an insertion assembly adapted to contain at least one fastener assembly, or adapted to contain at least two fastener assemblies, wherein the at least two fastener assemblies are aligned co-linearly in a distal-proximate orientation. The inner sheath assembly and the insertion assembly may further comprise dispensing means to controllably deliver an individual fastener assembly to secure the surgical component to the vessel. The fastener assembly may be located outside of the insertion assembly, or located within the insertion assembly. The fastener assemblies may further comprise a diluting tip at their distal end. The fastening assemblies may be attached to one another by a detachable means, wherein the detachable means may comprise at least one of mechanical force, electrical pulse, heat, dissolving a temporary connecting memberane, and shearing a temporary connecting membrane.

The present invention is also directed to a method of securing a surgical component to a vessel, comprising the steps of advancing a delivery sheath containing a catheter assembly through a vessel to a procedure specific area within the vessel, extending the catheter assembly such that an outer sheath of the catheter assembly extends from the delivery sheath, wherein an end portion of the outer sheath assumes an angular configuration, advancing an inner sheath from within the outer sheath such that the outer sheath contacts a surgical component at a location opposite to a point of contact of the inner sheath, further advancing the inner sheath such that the inner sheath applies sufficient pressure on the surgical component to push the surgical component firmly against the vessel, advancing an insertion assembly from within the inner sheath to create an aperture in the surgical component and the vessel through which a fastener assembly extends, advancing the insertion assembly and the fastener assembly through the aperture, and retracting the insertion assembly and the inner sheath such that the fastener assembly secures the surgical component to the vessel. The method according to the present invention may also comprise the steps of activating a laser fiber assembly, prior to advancing the insertion assembly and the fastener assembly through the aperture, to create the aperture through which the fastener assembly extends, or activating a piezo-electric device, prior to advancing the insertion assembly and the fastener assembly through the aperture, to create the aperture through which the fastener assembly extends.

The method according to the present invention may also include the steps of manipulating the catheter assembly within the vessel to another location, after retracting the insertion assembly and the inner sheath. The insertion assembly and the fastener assembly may advance through an aperture simultaneously, or the advancement of the insertion assembly through the aperture may precede the advancement of the fastener assembly through the aperture.

The present invention is also directed to a method of securing a surgical component to a vessel, the method comprising the steps of inserting a surgical component into a vessel at an entry site, moving the surgical component to a location within the vessel remote from the entry site, holding the surgical component in place within the vessel by a securing means, inserting a delivery catheter into the vessel, wherein the delivery catheter contains a fastening assembly, maneuvering the delivery catheter to a location in close proximity to the surgical component, deploying the fastening assembly to attach the surgical component to the vessel, manipulating the fastener assembly to secure the surgical component to the vessel, and removing the delivery catheter from the vessel. The surgical component, and/or an insertion assembly may be contained within the delivery catheter. The fastening assembly may be inserted into an aperture from the outside of the insertion assembly or from within the insertion assembly.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will now be described in conjunction with the following drawings in which like reference numerals designate like elements and wherein:

FIGS. 8a–e are perspective views of the delivery catheter assembly of FIG. 1, including multiple fastener assemblies during the process of inserting a fastener assembly to secure the surgical component to the vessel wall;

DETAILED DESCRIPTION OF PREFERRED EMBODIMENTS

The following description of the preferred embodiment of the present invention is described, for purpose of example, in connection with the repair of an aortic aneurysm. It is contemplated that the embodiments described herein are capable of use in the repair of other vessels and in other procedures. Thus, it is intended that the present invention cover the modifications and variations of the invention, provided they come within the scope of the appended claims and their equivalents.

Figure 1:
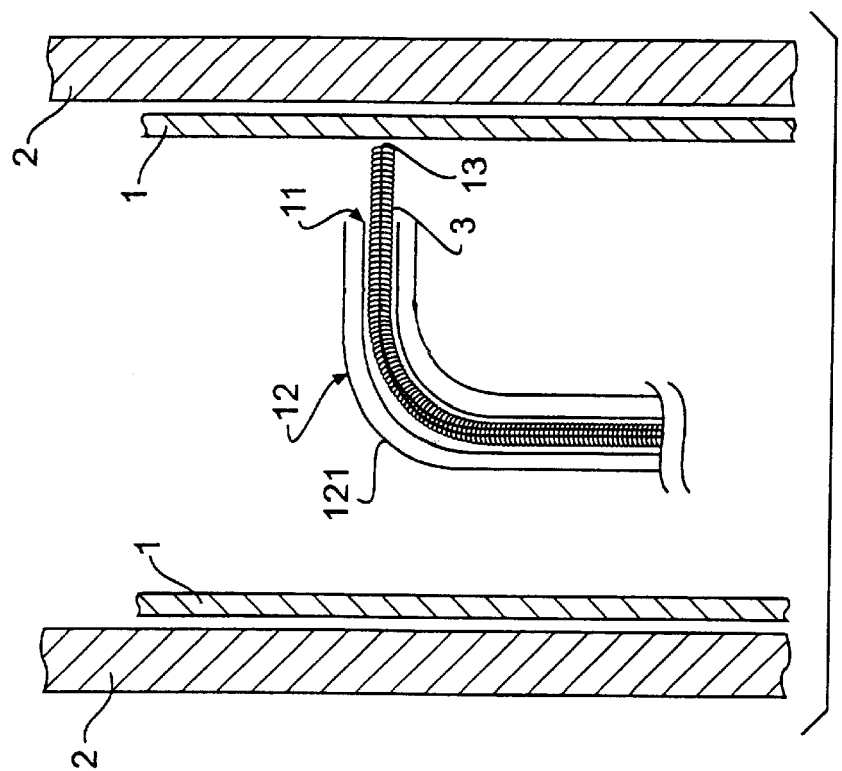
FIG. 1 is a perspective view of a delivery catheter assembly in accordance with the present invention, wherein the delivery catheter assembly is located within a vessel in an angled configuration.
Figure 4:
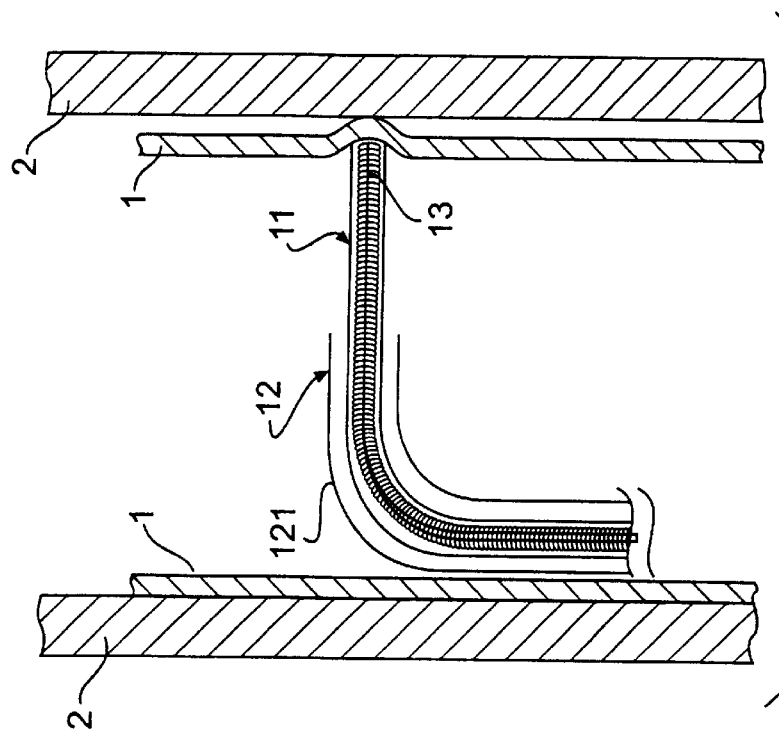
FIG. 4 is a perspective view of the delivery catheter assembly of FIG. 1 at the beginning of the process of inserting a fastener to secure a surgical component to a vessel wall.
Figure 6:
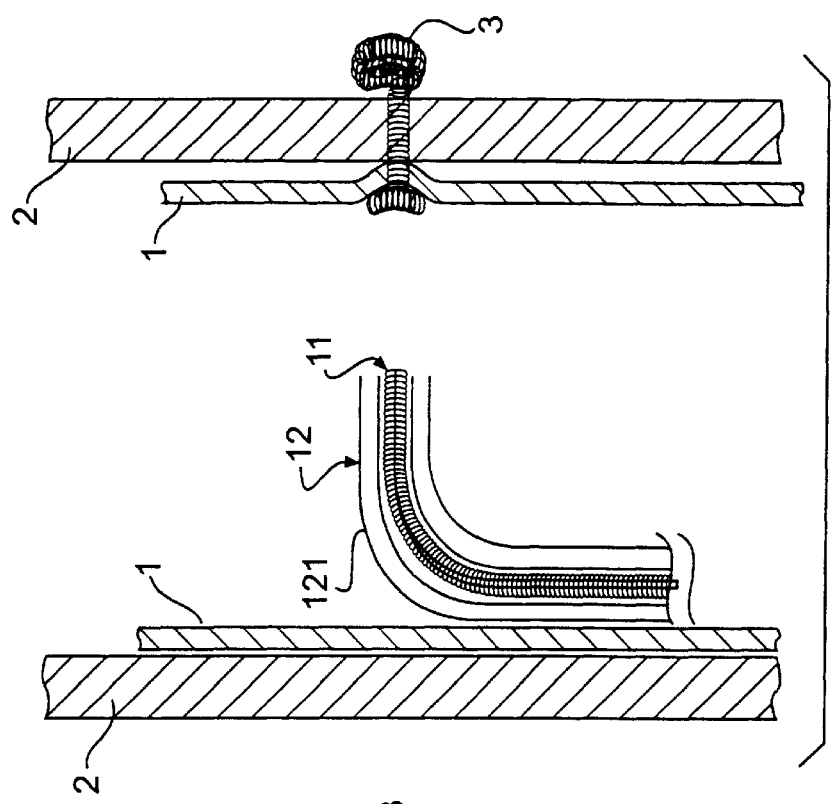
FIG. 6 is a perspective view of the delivery catheter assembly of FIG. 1 after the fastener assembly has secured the surgical component to the vessel wall.
Figure 5:
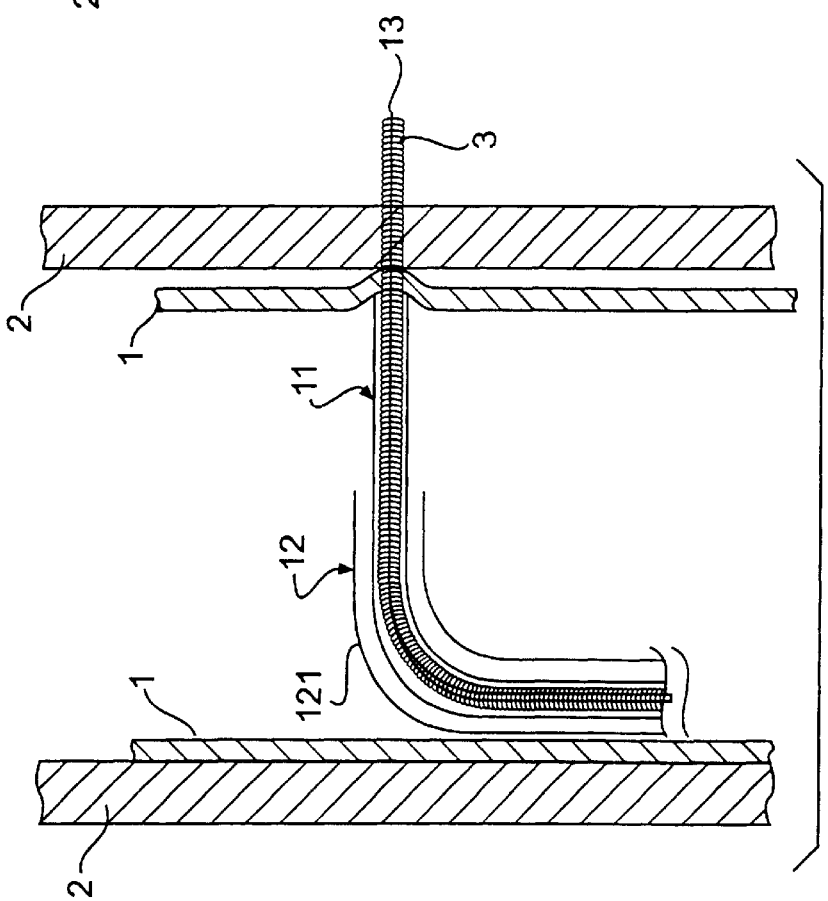
FIG. 5 is a perspective view of the delivery catheter assembly of FIG. 1 during the process of inserting a fastener to secure the surgical component to the vessel wall.

The delivery catheter assembly 10 will now be described in connection with FIGS. 1–6. The delivery catheter assembly 10 includes an inner sheath 11 and an outer sheath 12. An insertion assembly 13 is located within the inner sheath 11, as shown in FIG. 1. The insertion assembly 13 preferably creates an aperture within a surgical component 1 and a vessel 2, as shown in FIGS. 4–6, such that a fastener assembly 3 may be inserted through the aperture to secure the surgical component 1 to the vessel 2, as shown in FIG. 6. As shown in FIGS. 1–9, more than one fastener assembly 3 may be contained in the inner sheath 11 aligned co-linearly in a distal-proximate orientation either located outside the insertion assembly 13 or within the insertion assembly 13.

The fastener assembly 3 is preferably a flexible fastener assembly that applies a force to secure the surgical component 1 to the vessel 2, as disclosed in the following U.S. patent applications: U.S. Provisional Patent Application No. 60/181,230, filed Feb. 9, 2000; U.S. patent application Ser. No. 09/442,768, filed Nov. 18, 1999; U.S. patent application Ser. No. 09/213,233, filed Dec. 17,1998, now U.S. Pat. No. 5,997,556; U.S. patent application Ser. No. 08/958,524, filed Oct. 27,1997, now U.S. Pat. No. 5,957,940, U.S. patent application Ser. No. 08/896,415, filed Jul. 18,1997, now U.S. Pat. No. 5,944,750; and U.S. Provisional Patent Application No. 60/051,209, filed Jun. 30, 1997. The subject matter of these patent applications is incorporated herein specifically by reference.

The inner sheath 11 of the delivery catheter assembly 10 is movable with respect to the outer sheath 12. The delivery catheter assembly 10 is advanced to the surgical procedure specific area within the vessel 2 through a delivery sheath 4. The delivery catheter assembly 10 and the delivery sheath 4 have sufficient length such that the assembly 10 and sheath 4 may extend from either an axillary incision, a brachial incision or a femoral or common iliac arteriotomy to the procedure specific area within the vessel 2.

The catheter assembly 10 has an end portion 121 having an angular configuration, as shown in FIGS. 1–6. The catheter assembly 10 is flexible such that it may be advanced through the delivery sheath 4. The outer sheath 12 is formed from a suitable material that permits the end portion 121 to be flexed to maintain its angular configuration during the process of inserting a fastener 3 through the surgical component 1 and the vessel 2, as show in FIGS. 1–6. The outer sheath 12 preferably has a braided construction.

Figure 7:
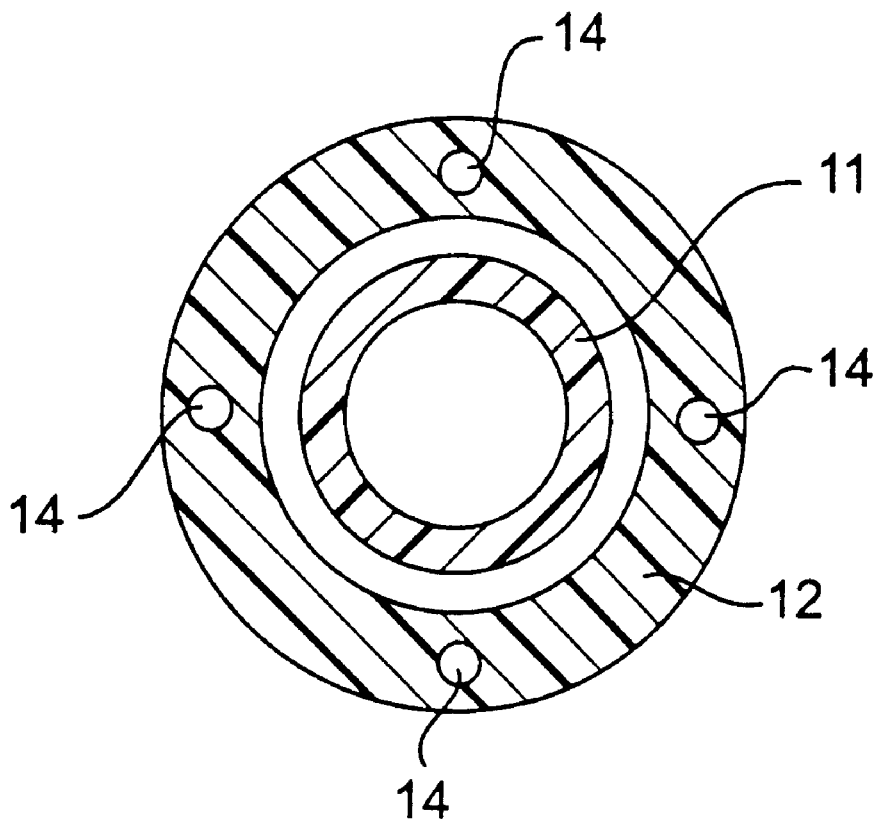
FIG. 7 is a cross sectional view of the outer sheath 12 of the catheter assembly in accordance with the present invention.
Figure 9A:
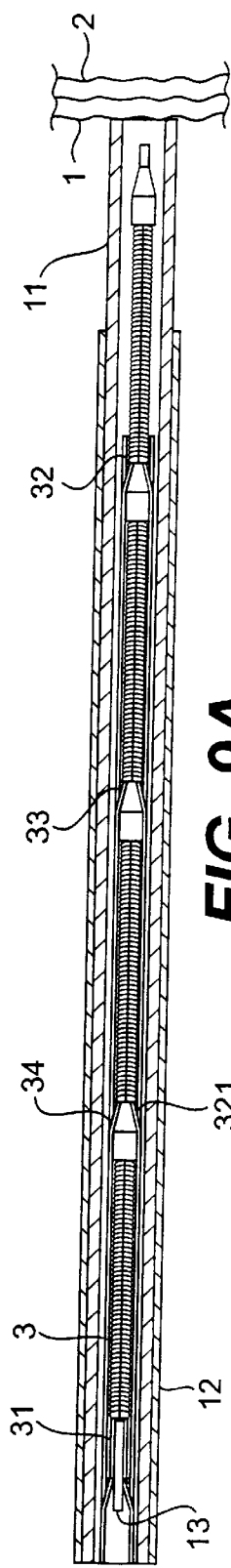
FIGS. 9a–d are perspective views of the delivery catheter assembly of FIG. 8 in accordance with another embodiment of the present invention.
Figure 9B:
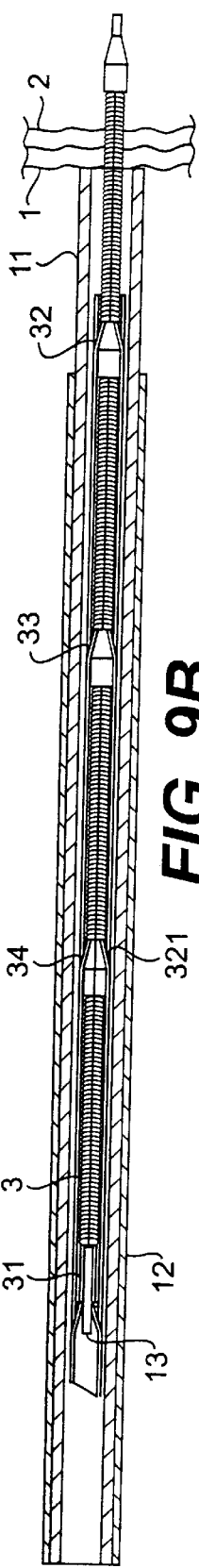
Figure 9C:
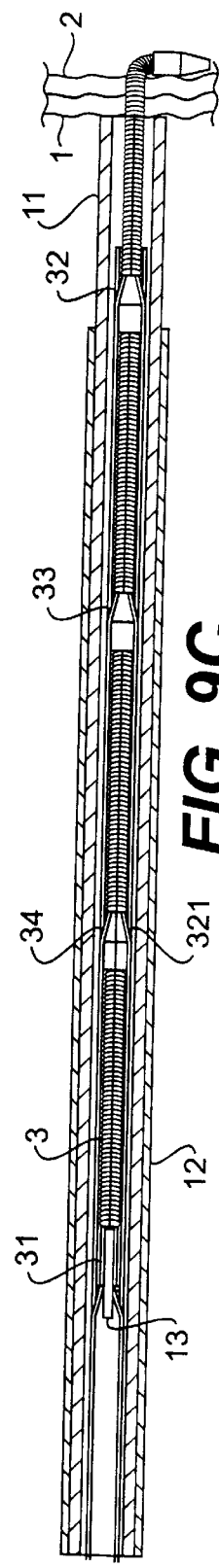
Figure 9D:
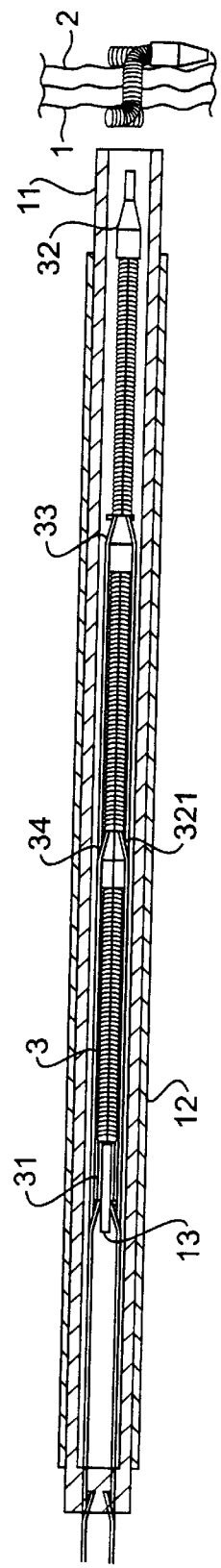

The angular configuration of the end portion 121 is achieved with at least one pull wire 14 positioned within the outer sheath 12, as shown in FIG. 7. The end portion of the outer sheath 12 is deflected when the at least one pull wire 14 is tensioned. Each of the at least one wire 14 extends through the outer sheath 12. A free end portion of each pull wire 14 exits the outer sheath 12 at a point that is located outside the body of the patient during the surgical procedure. The free end portion of the pull wire 14 maybe manipulated/tensioned by the surgeon by hand. Alternatively, the free end portion of the pull wire 14 may be connected to a control assembly (not shown) for operation by the surgeon. Each pull wire 14 is separated from the exterior of the deflectable tip section by a wall thickness less than 0.010". This permits deflection of the end portion of the outer sheath 12 when one of the pull wires 14 are tensioned. Each pull wire 14 is preferably surrounded by an elastomeric sleeve of a polymeric material of a recoverable elongation of 500–1000%. Examples of such materials are polyurethane and silicone elastomer. The pull wires 14 are protected from tissue abrasion by the elastomeric sleeve. Further, this construction prevents the release of fragments in the vessel in the event a pull wire fails. Also, the failure of a pull wire does not produce a permanently curved shape that would be difficult to remove from the vessel. The elastomeric sleeve, the inner sheath 11 and the outer sheath 12 provide a driving force that allows the tip to straighten once when the tension on the pull wire 14 is relaxed.

The outer sheath 12 preferably has a braided construction with increasing less durometer in the distal direction in order to optimize torque transmission. The lesser durometer sections of the outer sheath 12 correspond to areas where the catheter is expected to negotiate bends in the anatomy. These more flexible areas of the outer sheath 12 can more efficiently transmit torque around a bend than stiffer high durometer areas. Typical materials used to form the outer sheath 12 may be polyether amide compounds and polyurethane, or any other suitable material. Each pull wire 14 permits deflection of the end portion of the outer sheath 12 in a single direction. In a preferred embodiment, the outer sheath 12 includes a plurality of pull wires 14, as shown in FIG. 7, to permit multi-directional deflection of the end portion of the outer sheath 12. The wire 14 extends out of the circumferential envelope of catheter diameter when the wire 14 is under tension to effect tip deflection. The outer sheath 12 being deflected out of the normal diameter of the catheter.

Figure 2:
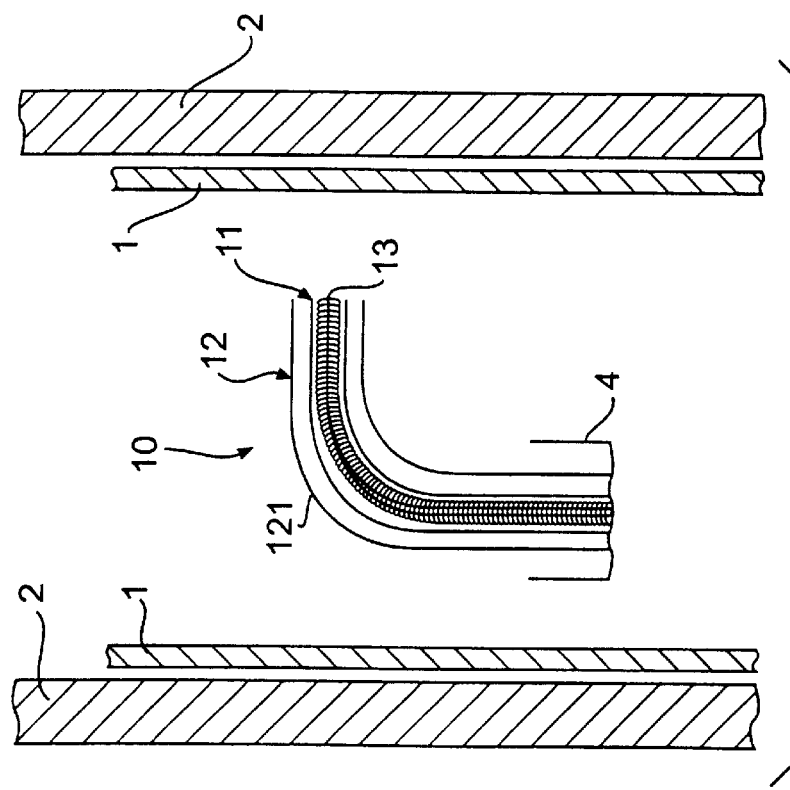
FIG. 2 is a perspective view of the delivery catheter assembly of FIG. 1, wherein the inner sheath of the catheter assembly is advanced from the outer sheath.
Figure 3:
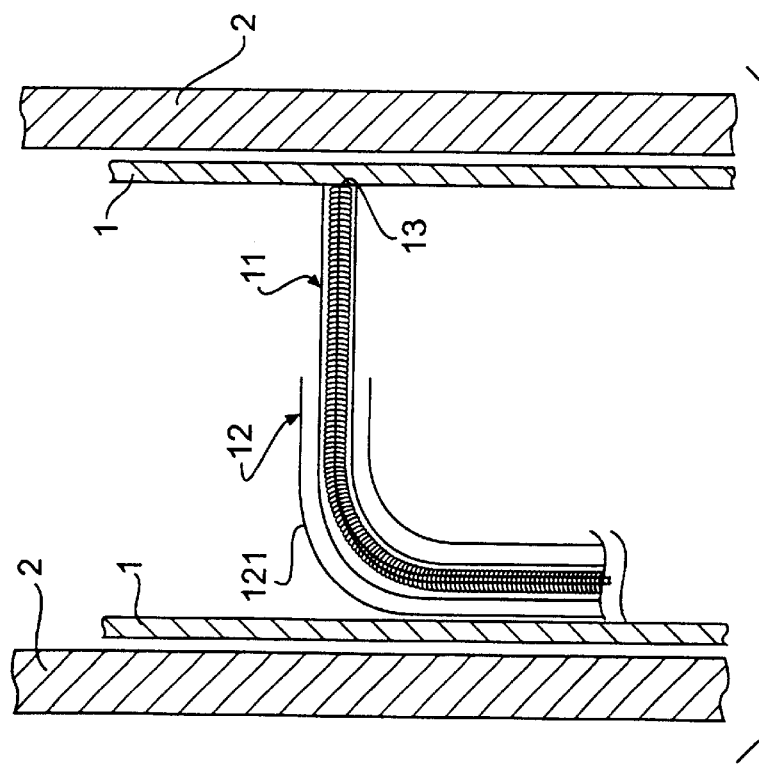
FIG. 3 is a perspective view of the delivery catheter assembly of FIG. 1, wherein the inner sheath is in a fully extended position within the vessel.

The operation of the delivery catheter assembly 10 will now be described. The delivery sheath 4 and delivery catheter assembly 10 are advanced through the vessel 2 to the procedure specific area within the vessel 2. The catheter assembly 10 is the extended such that the end portion 121 of the catheter assembly 10 extends from the sheath 4. The end portion 121 then assumes its angular configuration, as shown in FIG. 1, by manipulating one of the pull wires 14. The inner sheath 11 is then advanced such that it extends to contact the surgical component 1, as shown in FIG. 2. The inner sheath 11 is further advanced such that the outer sheath 12 contacts the surgical component 1 at a location opposite to the point of contact of the inner sheath 11, as shown in FIG. 3. The inner sheath 11 is still further advanced such that it applies sufficient pressure on the surgical component 1 to push the surgical component 1 firmly against the vessel 2, as shown in FIG. 4. The insertion assembly 13 is then activated and advanced to create an aperture in the surgical component 1 and the vessel 2 through which the fastener assembly 3 extends, as shown in FIG. 5. The insertion assembly 13 preferably includes a laser fiber assembly that is capable of creating an aperture through which the fastener assembly 3 is inserted to secure the surgical component 1 to the vessel 2. The insertion assembly 13 in accordance with the present invention is not limited to a laser fiber assembly; rather, a piezoelectric penetration device, as disclosed in U.S. Pat. Nos. 5,997,556, 5,957,940 and 5,944,750 and the embodiments disclosed therein are considered to be well within the scope of the present invention.

The insertion assembly 13 advances through the aperture that it has created as well as a fastener assembly 3, as shown in FIG. 5. The advancement of the fastener assembly 3 may occur simultaneously with the advancement of the insertion assembly 13, or may follow the advancement of the insertion assembly 13. In addition, the fastener assembly 3 may be located around the outside of insertion assembly 13, or the fastener assembly 3 may be located within a hollow core of insertion assembly 13. The insertion assembly 13 advances a fixed distance through and beyond the vessel 2 such that one portion of the fastener assembly 3 is located on one side of the vessel 2 and another portion of the fastener assembly 3 is located on an opposite side of the surgical component 1. The insertion assembly 13 and the inner sheath 11 are then retracted to the position shown in FIG. 6 leaving behind the fastener assembly 3 in an inserted position. The catheter assembly 10 is then manipulated within the vessel 2 to another location whereby the process of inserting a fastener assembly 3 is repeated to secure the surgical component 1 to the vessel 2. The catheter assembly 10 may be manipulated by releasing the tension in one of the pull wires 14 and applying tension to another pull wire 14. Thus changing the deflection of the outer sheath 12.

The operation of the catheter assembly 10 is controlled by a controller, such as for example, a hand controller (not shown) located outside the body.

According to another embodiment of the present invention, the fastener assembly 3 is designed such that it is possible to place a string of fastener assemblies 3 in a continuous head to tail fashion within the inner sheath 11 as shown in FIG. 8. This arrangement provides a method of sequentially dispensing multiple fastener assemblies 3 to attach the surgical component 1 to the vessel 2. The methods described herein permit more than one fastener assembly 3 to be contained in the inner sheath 11 and to be sequentially advanced into the surgical component 1 and vessel 2. The fastener assemblies 3 may be deployed from around the insertion assembly 13, or may be deployed from within a hollow insertion assembly 13.

FIG. 8 illustrates a method according to the present invention. FIG. 8a depicts the positioning of the delivery catheter assembly in preparation for employing the fastening assembly 3. FIG. 8b illustrates the creation of a treatment specific hole in the surgical component 1 and vessel 2 by an insertion assembly 13. A fastener assembly 3 may advance simultaneously with the insertion assembly 13, or may advance into the treatment specific hole following the advancement, and prior to the retraction, of the insertion assembly 13. Once the distal end of the fastener assembly 3 is inserted through the surgical component 1 and vessel 2 through the treatment specific hole, the insertion assembly 13 is retracted as shown in FIG. 8c. A backstop tube 31, located at the proximal end of the string of fastener assemblies 3, holds the linear position of the fastener assemblies 3 and maintains their position while the insertion assembly 13 is retracted. Upon retraction of the insertion assembly 13 the fastener assembly 3 assumes a secondary orientation, securely attaching the surgical component 1 to the vessel 2 as shown in FIGS. 8c and d. FIG. 8e illustrates a view of the attached fastener assembly from the outside of the vessel.

FIG. 9 illustrates an alternative method for advancing multiple fastener assemblies 3 in relation to the insertion assembly 13 according to an embodiment of the present invention. The method is similar to that described in FIGS. 8a–d. This method incorporates a pusher tube assembly 32 and an o-ring assembly 33. The pusher tube assembly 32 is responsible for maintaining the position of each fastener assembly 3. The pusher tube assembly 32 further includes spring loaded tabs 321 that seat securely to the proximal edge of each fastener assembly 3. The spring loaded tabs 321 engage an o-ring assembly 33 which ensures that a positive and reproducible engagement takes place between the pusher tube 32 and the edge of the fastener assembly 3. FIG. 9 illustrates two spring loaded tabs 321 per fastener assembly 3. The spring loaded tabs 321 open during fastener assembly 3 advancement thereby allowing the next fastener assembly 3 into position.

The above methods describe an embodiment of the present invention in which the fastener assemblies 3 are loaded as a continuous string in which the head of one fastener assembly 3 immediately abuts the tail of another fastener assembly 3. The fastener assemblies 3 may be separated from one another at the point of deployment by any number of means. These means include, but are not limited to, those means discussed above, as well as retracting the string of fastener assemblies 3 once the deployed fastener is correctly positioned within the surgical component 1 and vessel 2 such that a thin connecting membrane between the deployed fastener assembly 3 and the next fastener assembly 3 located in the inner sheath 11 is sheared. Methods of shearing may include, but are not limited to, mechanical force, application of an appropriately controlled electrical pulse, the application of heat, or by dissolving a temporary connecting membrane. The fastener assembly 3 inserted into the surgical component 1 and the vessel 2 may be held in place by a number of different methods, including but not limited to, threading, bonding, rehydration, thermal changes, deformation, expansion, friction, or torsion.

FIGS. 8–11 illustrate an embodiment of the fastener assembly 3 according to the present invention. A method of facilitating the insertion of fastener assemblies 3 includes a dilating tip 34 that is secured to the leading edge of the fastener assembly 3. During penetration of the surgical component 1 and vessel 2 the presence of dilating tip 34 may reduce the force required to insert the fastener assembly 3.

Figure 10:
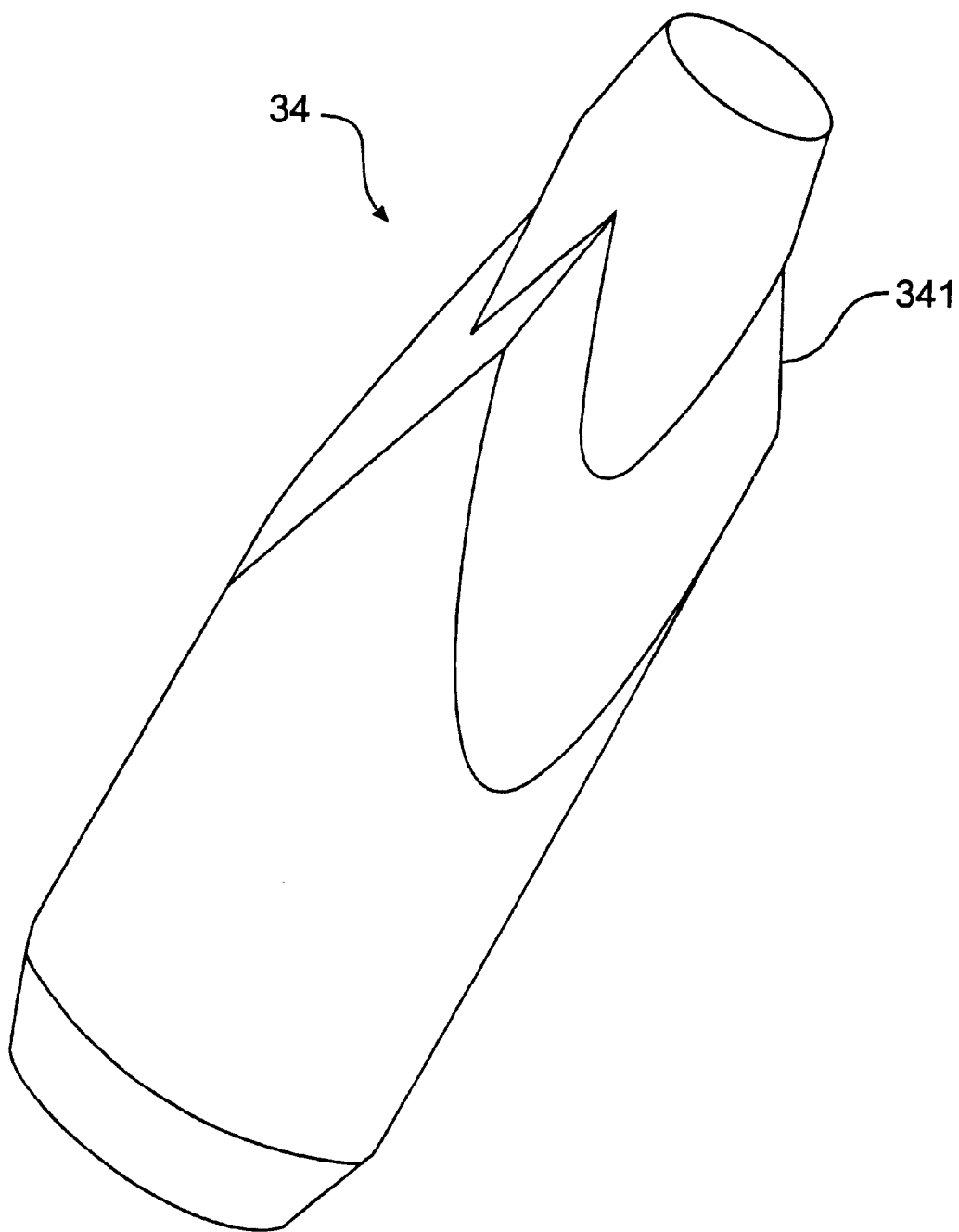
FIG. 10 illustrates a dilating tip according to an embodiment of the present invention.
Figure 11:
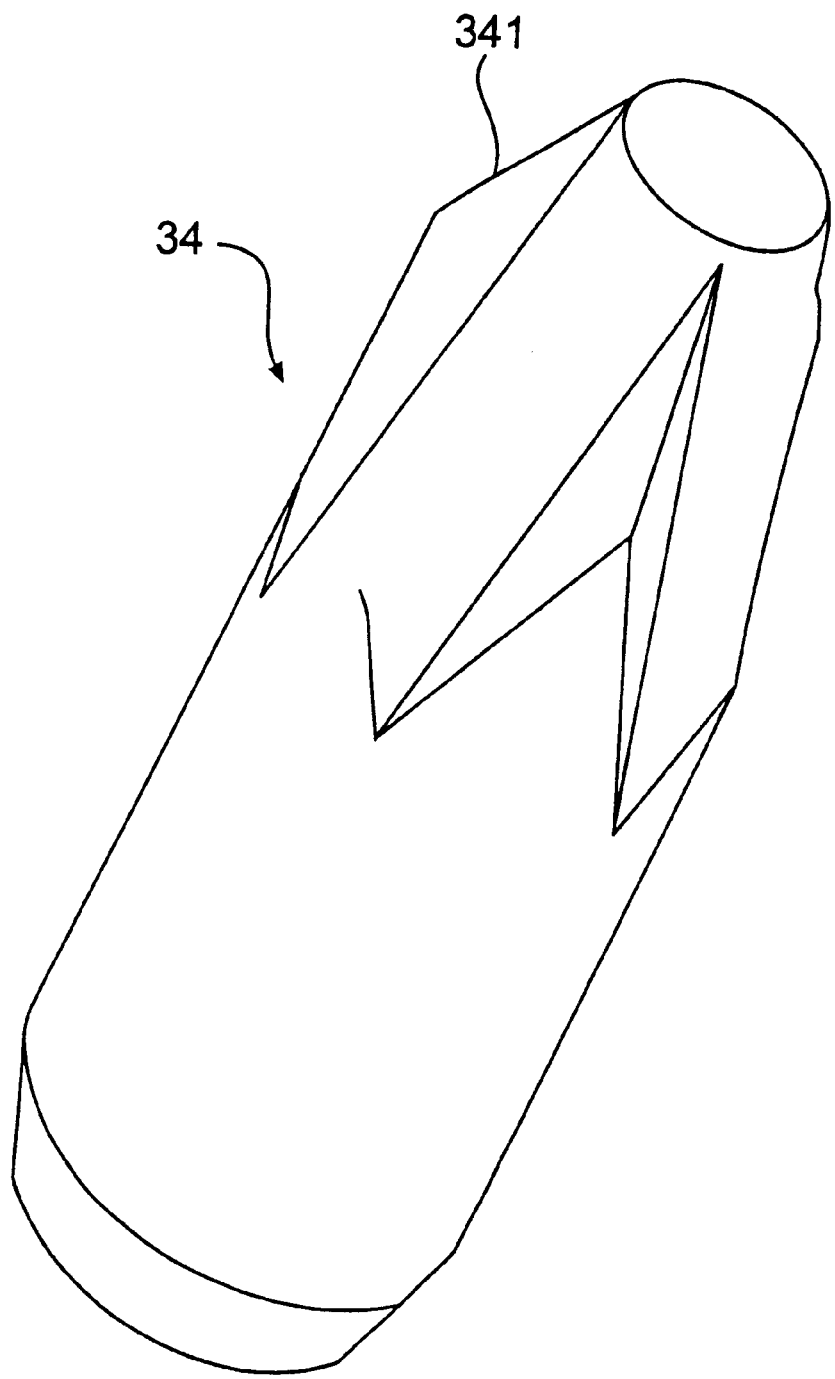
FIG. 11 illustrates a dilating tip according to an alternative embodiment of the present invention.

FIGS. 10 and 11 illustrate a dilating tip 34 illustrating at least one cutting edge 341 on the leading end of the dilating tip 34. The cutting edge 341 facilitates the insertion of fastener assembly 3 into the surgical component 1 and vessel 2. The cutting edge 341 may be ground into the surgical fastener 3 or can be a feature molded into fastener assembly 3. The dilating tip 34 may be constructed of commonly known surgical implant materials including, but not limited to, bioresorbables, metals such as MP-35N titianium, etc., and ultrahigh molecular weight polyurethane, UHMWPE, or any other suitable material. The dilating tips 34 are designed to be securely fixed to the leading edge fastener assembly 3.

While this invention has been described in conjunction with specific embodiments thereof, it is evident that many alternatives, modifications and variations will be apparent to those skilled in the art. Although the present invention is described in connection with securing a surgical component 1, which may be a graft assembly, to a vessel, which may be an aortic wall, the present invention is not limited to securing a surgical component to a vessel; rather, it is contemplated that the present invention may be used in connection with securing a vessel to another vessel, tissue to tissue, surgical components to surgical components and any variations thereof. Furthermore, it is contemplated that the delivery catheter assembly 10 may be used to deliver and/or advance other surgical devices including but not limited to a visualization device of other monitoring equipment, rather than the insertion assembly 13. Accordingly, the preferred embodiments of the invention as set forth herein are intended to be illustrative, not limiting. Various changes may be made without departing from the spirit and scope of the invention as defined in the following claims.

What is claimed is:

1. A delivery catheter assembly for advancing a surgical device to a desired location within a vessel during a surgical procedure, said delivery catheter assembly comprising:
   an inner sheath assembly through which the surgical device is advanced to the desired location within the vessel; and
   an outer sheath assembly surrounding said inner sheath assembly, wherein at least one of said inner sheath assembly and said outer sheath assembly having an angular configuration an insertion assembly located within said inner sheath assembly for securing the surgical component to the vessel.

2. The delivery catheter assembly according to claim 1, wherein said outer sheath assembly includes adjusting means for creating said angular configuration.

3. The delivery catheter assembly according to claim 2, wherein said adjusting means includes at least one pull wire located within said outer sheath assembly.

4. The delivery catheter assembly according to claim 2, wherein said adjusting means permits multi-directional manipulation of said outer sheath assembly.

5. The delivery catheter assembly according to claim 1, wherein said inner sheath assembly is movable with respect to said outer sheath assembly.

6. The delivery catheter assembly according to claim 5, wherein said inner sheath assembly is capable of moving between an extended position and a retracted position at the predetermined time during the surgical procedure.

7. An assembly for use in securing a surgical component to a vessel during a surgical procedure, said assembly comprising:
   a delivery catheter assembly having an inner sheath assembly through which a surgical device is advanced to a desired location within the vessel, and an outer sheath assembly surrounding said inner sheath assembly, wherein at least one of said inner sheath assembly and said outer sheath assembly having an angular configuration at a predetermined time during the surgical procedure; and
   an fastener assembly located within said inner sheath assembly for securing the surgical component to the vessel.

8. The assembly according to claim 7, wherein said insertion assembly includes means for creating an aperture within the surgical component and the vessel such that a fastener assembly may be inserted there through.

9. The assembly according to claim 7, further comprising advancing means for advancing said delivery catheter assembly to the desired location.

10. The assembly according to claim 9, wherein said advancing means includes a delivery sheath, wherein said catheter assembly is slidably received within said delivery sheath.

11. The assembly according to claim 7, wherein said outer sheath assembly includes adjusting means for creating said angular configuration.

12. The assembly according to claim 7, wherein adjusting means permits multi-directional manipulation of said outer sheath assembly.

13. The assembly according to claim 7, wherein said inner sheath assembly and said insertion assembly are adapted to contain at least one fastener assembly.

14. The assembly according to claim 7, wherein said inner sheath assembly and said insertion assembly are adapted to contain at least two fastener assemblies, wherein said at least two fastener assemblies are aligned co-linearly in a distal-proximate orientation.

15. The assembly according to claim 14, wherein said inner sheath assembly and said insertion assembly further comprise dispensing means to controllably deliver an individual fastener assembly to secure the surgical component to the vessel.

16. The assembly according to claim 13, wherein said at least one fastener assembly is located outside of said insertion assembly.

17. The assembly according to claim 13, wherein said at least one fastener assembly is located within said insertion assembly.

18. A method of securing a surgical component to a vessel, comprising the steps of:
   advancing a delivery sheath containing a catheter assembly through a vessel to a procedure specific area within the vessel;
   extending said catheter assembly such that an outer sheath of said catheter assembly extends from said delivery sheath, wherein an end portion of said outer sheath assumes an angular configuration;
   advancing an inner sheath from within said outer sheath such that said outer sheath contacts a surgical component at a location opposite to a point of contact of said inner sheath;
   further advancing said inner sheath such that said inner sheath applies sufficient pressure on the surgical component to push the surgical component firmly against the vessel;
   advancing an insertion assembly from within said inner sheath to create an aperture in the surgical component and the vessel through which a fastener assembly extends;

advancing said insertion assembly and said fastener assembly through said aperture;

retracting said insertion assembly and said inner sheath such that said fastener assembly secures the surgical component to the vessel.

19. The method of delivering a catheter assembly according to claim 18, further comprising the step of:

activating a laser fiber assembly, prior to advancing said insertion assembly and said fastener assembly through said aperture, to create said aperture through which said fastener assembly extends.

20. The method of delivering a catheter assembly according to claim 18, further comprising the step of:

activating a piezoelectric device, prior to advancing said insertion assembly and said fastener assembly through said aperture, to create said aperture through which said fastener assembly extends.

21. The method of delivering a catheter assembly according to claim 18, further comprising the step of:

manipulating said catheter assembly within said vessel to another location, after retracting said insertion assembly and said inner sheath.

22. The method of securing a surgical component to a vessel according to claim 18, wherein said insertion assembly and said fastener assembly are advanced through said aperture simultaneously.

23. The method of securing a surgical component to a vessel according to claim 18, wherein advancement of said insertion assembly through the aperture precedes the advancement of said fastener assembly through the aperture.

24. An assembly for use in securing a surgical component to a vessel during a surgical procedure, said assembly comprising:

a delivery catheter assembly having an inner sheath assembly through which the surgical device is advanced to a desired location within the vessel, and an outer sheath assembly surrounding said inner sheath assembly, wherein at least one of said inner sheath assembly and said outer sheath assembly having an angular configuration at a predetermined time during the surgical procedure;

an insertion assembly located within said inner sheath assembly for securing the surgical component to the vessel; and at least two fastener assemblies located within the inner sheath assembly.

25. The assembly according to claim 24, wherein each of said at least two fastener assemblies further comprise a diluting tip at the distal end.

26. The assembly according to claim 24, wherein said at least two fastening assemblies are attached to one another by a detachable means.

27. The assembly according to claim 26, wherein said detachable means comprises at least one of mechanical force, electrical pulse, heat, dissolving a temporary connecting memberane, and shearing a temporary connecting membrane.

28. A method of securing a surgical component to a vessel, said method comprising the steps of:

inserting a surgical component into a vessel at an entry site;

moving the surgical component to a location within the vessel remote from the entry site;

holding the surgical component in place within the vessel by a securing means;

inserting a delivery catheter into the vessel, wherein said delivery catheter contains a fastening assembly;

maneuvering said delivery catheter to a location in close proximity to the surgical component;

deploying said fastening assembly to attach the surgical component to the vessel;

manipulating the fastener assembly to secure the surgical component to the vessel; and removing said delivery catheter from the vessel.

29. The method according to claim 28, wherein the surgical component is contained within said delivery catheter.

30. The method according to claim 28, wherein an insertion assembly is contained within said delivery catheter.

31. The method according to claim 30, wherein said insertion assembly creates an aperture in the surgical component and the vessel.

32. The method according to claim 30, wherein said fastening assembly is inserted into the aperture from the outside of said insertion assembly.

33. The method according to claim 30, wherein said fastening assembly is inserted into the aperture from within said insertion assembly.

* * * * *